United States Patent
Shaffer et al.

(10) Patent No.: US 10,299,520 B1
(45) Date of Patent: May 28, 2019

(54) FABRIC-BASED ITEMS WITH ENVIRONMENTAL CONTROL ELEMENTS

(71) Applicant: Apple Inc., Cupertino, CA (US)

(72) Inventors: Benjamin A. Shaffer, Cupertino, CA (US); James H. Foster, Cupertino, CA (US)

(73) Assignee: Apple Inc., Cupertino, CA (US)

( * ) Notice: Subject to any disclaimer, the term of this patent is extended or adjusted under 35 U.S.C. 154(b) by 771 days.

(21) Appl. No.: 14/824,505

(22) Filed: Aug. 12, 2015

Related U.S. Application Data

(60) Provisional application No. 62/036,532, filed on Aug. 12, 2014.

(51) Int. Cl.
| | | |
|---|---|---|
| *H05B 3/34* | (2006.01) | |
| *A41D 13/005* | (2006.01) | |
| *A61B 5/00* | (2006.01) | |
| *A61B 5/0205* | (2006.01) | |

(52) U.S. Cl.
CPC ..... *A41D 13/0053* (2013.01); *A41D 13/0051* (2013.01); *A61B 5/02055* (2013.01); *A61B 5/6804* (2013.01); *A61B 5/6893* (2013.01); *H05B 3/347* (2013.01); *H05B 2203/016* (2013.01)

(58) Field of Classification Search
None
See application file for complete search history.

(56) References Cited

U.S. PATENT DOCUMENTS

| | | | |
|---|---|---|---|
| 5,105,067 A * | 4/1992 | Brekkestran | G05D 23/2401 2/69 |
| 6,713,733 B2 | 3/2004 | Kochman et al. | |
| 8,008,606 B2 * | 8/2011 | Kaiserman | A43B 7/04 219/211 |
| 8,308,489 B2 | 11/2012 | Lee et al. | |
| 8,397,517 B2 | 3/2013 | Monk | |
| 10,212,763 B2 * | 2/2019 | Kurley | H05B 3/146 |
| 2005/0061801 A1 * | 3/2005 | Kuo | H05B 3/347 219/529 |
| 2006/0280948 A1 * | 12/2006 | Moreshead | B32B 5/024 428/411.1 |
| 2007/0199137 A1 | 8/2007 | Numes Ramos De Carvalho et al. | |
| 2008/0083721 A1 * | 4/2008 | Kaiserman | A43B 3/0005 219/211 |

(Continued)

*Primary Examiner* — Joseph M Pelham
(74) *Attorney, Agent, or Firm* — Treyz Law Group, P.C.; Kendall W. Abbasi

(57) ABSTRACT

A fabric-based item may adapt to and adjust the biometric state of an individual that is wearing or touching the fabric-based item. The fabric-based item may be a cover for a seat in a vehicle, an article of clothing, a wrist band, or other suitable fabric-based item. The fabric-based item may include one or more sensors that gather biometric information about the individual and one or more environmental control devices that adjust or maintain the environment around the individual based on the biometric information. The sensors may include temperature sensors, humidity sensors, pressure sensors, heart rate sensors, or other sensors that gather biometric information about the user. The environmental control elements may be used to control the temperature, humidity, airflow or other aspect of the environment around the individual based on the biometric state of the individual.

20 Claims, 9 Drawing Sheets

(56) References Cited

U.S. PATENT DOCUMENTS

| | | | |
|---|---|---|---|
| 2010/0173548 A1* | 7/2010 | Kuhn | C09D 11/52 |
| | | | 442/72 |
| 2011/0062134 A1* | 3/2011 | Lochtman | D06M 11/74 |
| | | | 219/201 |
| 2011/0127248 A1* | 6/2011 | Moreshead | D03D 1/0076 |
| | | | 219/209 |
| 2011/0128686 A1* | 6/2011 | Moreshead | D03D 1/0076 |
| | | | 361/679.01 |
| 2011/0130813 A1* | 6/2011 | Moreshead | A61F 13/00051 |
| | | | 607/112 |
| 2011/0282164 A1 | 11/2011 | Yang et al. | |
| 2011/0290785 A1* | 12/2011 | Schaeffer | B60N 2/5685 |
| | | | 219/538 |
| 2012/0318781 A1* | 12/2012 | Lavin, Jr. | A41D 13/005 |
| | | | 219/211 |
| 2013/0001212 A1* | 1/2013 | Mangoubi | H05B 1/0272 |
| | | | 219/211 |
| 2013/0186884 A1* | 7/2013 | Barfuss | B23P 11/00 |
| | | | 219/529 |
| 2013/0306614 A1* | 11/2013 | Fey, Jr. | A41D 1/00 |
| | | | 219/211 |
| 2015/0173445 A1* | 6/2015 | Gordon | F25B 21/04 |
| | | | 62/3.3 |
| 2015/0230524 A1 | 8/2015 | Stevens et al. | |
| 2017/0172227 A1* | 6/2017 | Fan | A41D 31/0038 |
| 2017/0209301 A1* | 7/2017 | DeSeve | A61F 7/007 |
| 2017/0332442 A1* | 11/2017 | Strecker | A41D 13/0051 |

\* cited by examiner

FABRIC-BASED ITEMS WITH ENVIRONMENTAL CONTROL ELEMENTS

This application claims the benefit of provisional patent application No. 62/036,532 filed on Aug. 12, 2014, which is hereby incorporated by reference herein in its entirety.

BACKGROUND

This relates generally to control systems and, more particularly, to fabrics with environmental control elements.

People often interact with fabric-based articles. For example, a user may have a fabric-based watch band that wraps around the user's wrist. Clothing articles may come into contact with a user's skin. A car seat in a vehicle may have a fabric-based cover that rests against the passenger's legs and back.

Conventional fabric-based articles do not adapt to a person's biometric profile. A person may find a fabric-based article to be comfortable and breathable when the person is at rest, but when emotionally stressed or physically active, the person may find the same article to be restrictive and excessively warm. A person's emotional or physical state can be negatively affected by a non-responsive fabric that does not adapt to the person's activity or biometric state.

It would therefore be desirable to be able to provide improved fabric-based items for adapting and responding to a user's biometric profile.

SUMMARY

A fabric-based item may adapt to and adjust the biometric state of an individual that is wearing or touching the fabric-based item. The fabric-based item may be a cover for a seat in a vehicle, an article of clothing, a wrist band for a watch, or other suitable fabric-based item.

The fabric-based item may include one or more sensors that gather biometric information about the individual and one or more environmental control devices that adjust or maintain the environment around the individual based on the biometric information. The sensors may include temperature sensors, humidity sensors, pressure sensors, heart rate sensors, or other sensors that gather biometric information about the user. The environmental control elements may include thermal haptic devices such as Peltier effect devices that are used to adjust the temperature of the fabric and thereby adjust the thermal sensations felt by the individual. Other environmental control elements that may be used to control the environment around the individual include humidity control elements, airflow control elements, odor absorbing elements, odor emitting elements, or other environmental control elements that can adjust the sensations felt by the individual.

Control circuitry may be configured to operate the environmental control elements in the fabric based on the biometric information gathered by the sensors in the fabric. The control circuitry may infer information about an individual's emotional state based on the biometric information gathered by the sensors. For example, elevated temperatures in certain regions of the body may be indicative of increased stress levels. The control circuitry may operate the environmental control elements based on the inferred emotional state of the individual. If desired, the control circuitry may attempt to induce a certain emotional state using the environmental control elements. For example, cooling elements in the fabric may be activated to cool certain areas of the individual's body, which may in turn lead to increased wakefulness.

DESCRIPTION

Fabric-based items such as clothing and seat covers may incorporate environmental control elements. The environmental control elements may provide different sensations to an individual who is wearing, sitting on, or otherwise near the fabric-based item. As an example, a cover for a car seat in a vehicle may include environmental control elements that regulate the environment around a passenger's body. The environmental control elements may respond to an individual's biometric profile. One or more sensors in the fabric-based item may gather information about an individual's biometric state and the environmental control elements may respond accordingly. The use of environmental control systems in vehicle interiors is sometimes described herein as an example. In general, environmental control elements may be used in any fabric-based item that comes close to an individual's body (e.g., a backpack or other bag, a couch, a wrist band, an article of clothing, etc.).

Figure 1:
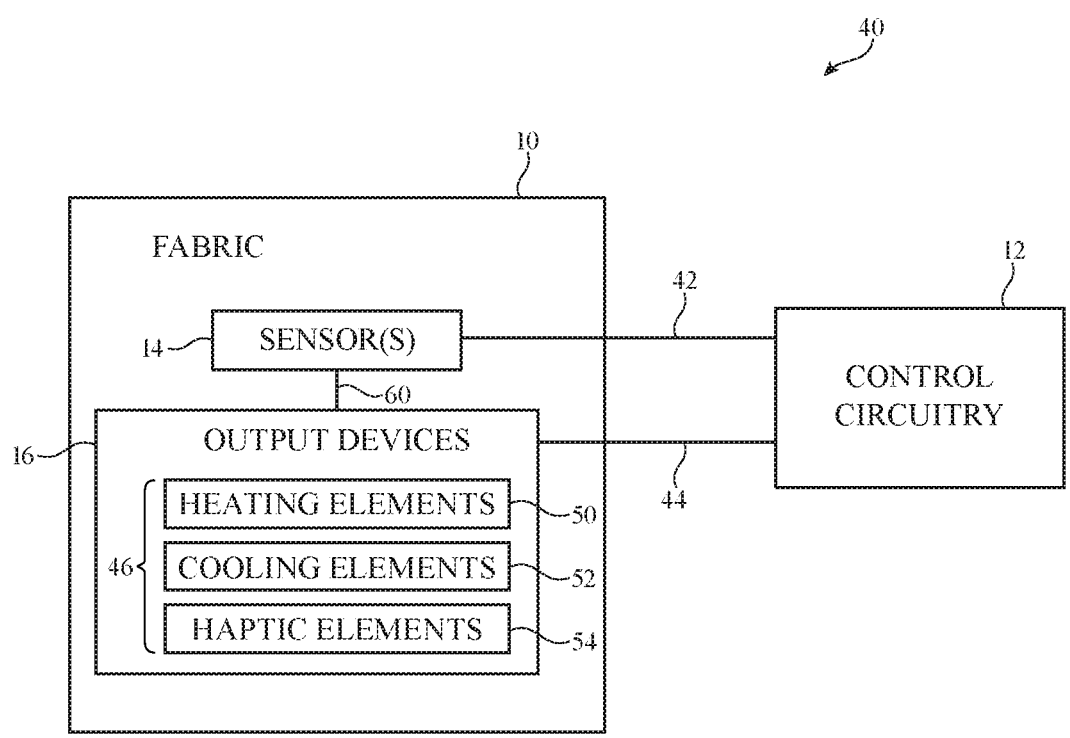
FIG. 1 is a schematic diagram of an illustrative system that may include fabric-based items in accordance with an embodiment.

An illustrative fabric-based system of the type that may include fabric with embedded sensors and environmental control elements or other components is shown in FIG. 1. Fabric-based system 40 may include fabric 10 and control circuitry 12.

Control circuitry 12 may include storage and processing circuitry that is configured to execute software. The software may control the operation of fabric 10 and/or components included in fabric 10. For example, code that is executed on control circuitry 12 may be used in controlling the temperature of fabric 10, may be used in adjusting vibrating elements or other mechanical devices in fabric 10, and/or may be otherwise used in adjusting the properties of fabric 10 and/or components embedded in fabric 10.

Control circuitry 12 may be implemented using one or more integrated circuits such as microprocessors, application specific integrated circuits, memory, and other storage and processing circuitry. If desired, control circuitry 12 may be included in an electronic device. For example, control circuitry 12 may be included in a computer that is integrated into a display such as a computer monitor, a laptop computer, a tablet computer, a somewhat smaller portable device such as a wrist-watch device, pendant device, or other wearable or miniature device, a cellular telephone, a media player, a tablet computer, a gaming device, a navigation device, a computer monitor, a television, or other electronic equipment. Control circuitry 12 may also be embedded within fabric 10 (e.g., within a thick portion of fabric 10, in a cushion or other item formed using fabric 10, in multiple locations distributed throughout fabric 10 and/or an item formed using fabric 10). In some embodiments, part of control circuitry 12 may be formed in a first item (e.g., an electronic device such as a portable electronic device, computer, tablet computer, etc.) and part of control circuitry 12 may be formed in a second item (e.g., an item of clothing formed from fabric 10, a cushion formed from fabric 10, etc.). Configurations in which control circuitry 12 is distributed among three or more items may also be used (e.g., three or more items such as clothing items, cushions or other furniture or seating items, electronic devices, etc.).

Fabric 10 may be a strand-based (e.g., fiber-based) structure with intertwined strands (e.g., fibers or other strands of material) that are woven, knitted, warp knitted, braided, or otherwise intertwined together to form a fabric material. Strands that are used to form fabric 10 may be formed natural fibers (e.g., cotton, linen, wool, etc.) or synthetic fibers (e.g., polyester, nylon, acrylic, spandex, etc.). Strands may be formed from one or more continuous filaments (e.g., continuous filaments that form a strand), untwisted bundles of continuous filaments, twisted bundles of non-continuous filaments, etc. Strands for fabric 10 can be formed from dielectric materials (e.g., plastic), metal or other conductive material (e.g., carbon fibers), plastic coated with metal, metal coated with plastic, or other conductive and/or non-conductive strands.

Fabric 10 may include embedded structures such as one or more sensors 14 and one or more output devices 16. As explained in detail below, sensors 14 can be integrated into fabric 10 or may be separate from fabric 10 (e.g., may be mounted to, carried by, or otherwise attached to fabric 10 without being integrated into fabric 10). Sensor signals gathered by sensors 14 may be conveyed to control circuitry 12 using path 42, and control circuitry 12 may issue control signals to output devices 16 using path 44.

Control circuitry 12 may be separate from fabric 10 or may be carried by or integral with fabric 10. In arrangements where all or part of control circuitry 12 is separate from fabric 10, the portion of control circuitry 12 that is separate from fabric 10 may communicate with fabric 10 over an electrical communications path or over a wireless communications path. Wireless communications paths may be implemented using wireless local area network protocols (e.g., IEEE 802.11 protocols—sometimes referred to as WiFi®), protocols for other short-range wireless communications links such as the Bluetooth® protocol, etc. Electrical communications path may be formed using conductive signal paths in one or more wires (e.g., fibers that are separate from fabric 10 and/or that are part of fabric 10) or may be formed using conductive traces on a substrate (e.g., a flexible printed circuit substrate, a rigid printed circuit substrate, or other suitable substrate).

Sensors 14 may include one or more sensors for gathering information such as biometric information about a user. For example, sensors 14 may be used to gather biometric information about a user that is wearing, sitting on, or otherwise contacting fabric 10. Sensors 14 may include temperature sensors, force sensors (e.g., piezoelectric sensors, resistive force sensors, capacitive force sensors, etc.), motion sensors (e.g., accelerometers, gyroscopes, etc.), switches or other mechanical sensors, moisture detectors, strain gauges, pressure sensors, microelectromechanical systems (MEMS) devices, capacitive sensors, touch sensors (e.g., touch sensor electrodes, drive and sense circuitry, etc.), resistance-based sensors, light-based sensors (e.g., infrared sensors), piezoelectric sensors, and/or acoustic-based sensors such as ultrasonic acoustic-based sensors (as examples). A user of system 40 may supply commands to sensors 14 (e.g., a user may supply a touch command or other input command) and/or sensors 14 may gather information about the environment in which system 40 is being used (e.g., information on the temperature of the surroundings of system 40, etc.), and/or sensors 14 may gather biometric data on the user (e.g., information on the temperature of part of the user's body, information on how much pressure is being exerted on fabric 10 by the user's body (e.g., when a user is sitting on fabric 10 or is otherwise in contact with fabric 10), or may gather other information about the user, input from the user, and/or information on the user's environment.

Information from sensors 14 may be used in gathering information on the way in which a user is wearing or touching fabric 10. For example, sensors 14 may detect one or more user conditions that control circuitry 12 may use to gather information about a user, including, for example, a user's temperature (e.g., skin temperature or body temperature), perspiration, blood flow, blood pressure, pulse (heart rate), or other biometric information. Information can be gathered through direct contact between sensors 14 and the user and/or the user's environment. For example, a temperature sensor in contact with a user may measure the user's temperature or a pressure sensor in contact with a portion of the skin of a user's body may measure pressures imposed on the sensor by the body. A heart rate sensor may be formed from one or more light sources (e.g., light emitting diodes) and one or more light detectors (e.g., photodiodes) that are used to detect the amount of blow flow in a region of the body (e.g., a user's wrist) adjacent to the fabric. Information can also be gathered indirectly. For example, a force sensor may detect that fabric 10 is being stretched and can conclude from this stretching that the user's body is imposing a force on fabric 10. Sensing arrangements that use combinations of direct and indirect sensing and/or that use one or more different types of sensor may also be used.

Control circuitry 12 may issue control signals to output devices 16 to provide output to a user (e.g., in response to information gathered by sensors 14 or other information such as information on the current time, output from an application program running on control circuitry 12 that is controlled by non-sensor input, output that is generated based on user commands, etc.).

Output devices 16 may include environmental control elements 46 that are capable of manipulating the environment around a user's body. Environmental control elements 46 may include thermal haptic elements such as heating elements 50 (e.g., resistive heating elements, thermoelectric (Peltier) effect heating devices, or other heating elements) and cooling elements 52 (e.g., refrigerant lines, thermoelectric coolant structures, thermoelectric (Peltier) cooling effect cooling elements, fans, or other cooling elements). Output device 16 may include mechanical components such as mechanical haptic elements 54 (e.g., an electromechanical actuator such as a haptic feedback device, a vibrator for issuing alerts, a device for imparting other vibrations or motions to fabric 10, actuators based on shape memory metals, etc.).

Components such as heating elements 50 and cooling elements 52 may be used to control the temperature of fabric 10 and/or the amount of heat conduction through fabric 10. These components may therefore sometimes be referred to as temperature control elements or temperature management components. If desired, temperature control elements may be implemented using elements that heat or cool fabric 10, may be implemented using elements that provide heating or cooling directly to a user, or may be implemented using elements that alter the thermal properties of fabric 10. For example, heating and cooling may be achieved by adjusting the breathability of fabric 10 (e.g., by adjusting the density of threads in fabric 10, by stretching or shrinking fabric 10, by aligning openings in two layers of fabric in fabric 10, by opening and/or closing air ports or other openings in fabric 10, etc.). Methods of adjusting the breathability of fabric 10 are described in detail in connection with FIG. 4.

Output devices 16 may provide output to a user by changing the properties of fabric 10. For example, fabric 10 may be heated using heating elements 50, cooled using cooling elements 52, and vibrated using actuators such as haptic elements 54. Other types of output may be provided using output devices 16. For example, fabric 10 may be configured to stretch (e.g., to provide greater breathability) or shrink (e.g., to provide compression to an area on the user's body). In general, output devices 16 may provide any suitable type of output to change a user's experience (e.g., to adjust blood circulation, to alert a user, to adjust skin or body temperature, to adjust pleasurability, etc.).

In additional to heating elements 50 and cooling elements 52, environmental control elements 46 may include airflow control elements, filters, humidity control elements, odor-absorbing and/or odor-emitting elements, or other suitable elements for providing different sensations to an individual and controlling the environment around an individual's body and/or near the individual's skin. Because environmental control elements 46 may sometimes use thermal effects to induce a tactile sensation for the user, environmental control elements 46 may sometimes be referred to as thermal haptic elements.

Output devices 16 may be controlled based on information from sensors 14 or may be controlled independently of sensors 14. For example, fabric 10 may be pre-programmed or manually operated (e.g., fabric 10 may be manually controlled remotely or locally by control circuitry 12) to activate output devices 16 in a desired fashion.

If desired, control circuitry 12 may be omitted and fabric 10 may be configured to operate automatically. In this type of arrangement, sensors 14 and output devices 16 may communicate directly over path 60 and output devices 16 may be automatically activated or deactivated based on gathered sensor signals. As an example, cooling elements 52 may automatically be activated when sensors 14 detect perspiration (e.g., when a humidity sensor or moisture sensor detects humidity (moisture) levels over a threshold).

Control circuitry 12 may use sensor 14 to gather information about an individual's biometric state and may use environmental control elements 46 to induce a desired effect on the individual's biometric state. In some scenarios, an individual's biometric state may be linked to the individual's emotional state. Changes in body temperature may be linked to (e.g., may be caused by or may be the cause of) changes in emotional state. As examples, elevated temperatures in certain areas of the body may be indicative of stress. Cooling certain areas of the body may lead to increased wakefulness.

If desired, control circuitry 12 may use sensors 14 and environmental control elements 46 to infer and induce changes in an individual's emotional state. For example, control circuitry 12 may use biometric information from sensors 14 (e.g., information on the user's skin temperature at one or more locations on the user's body, the user's heart rate, the user's movement, etc.) to make inferences about a user's emotional state. Similarly, control circuitry 12 may use environmental control elements 46 to provide an environment that may induce emotional or physical changes for the user.

If desired, control circuitry 12 may operate environmental control elements 46 based on the inferred emotional state of an individual. For example, control circuitry 12 may infer a user's emotional state based on body temperature information gathered by sensors 14. Control circuitry 12 may activate one or more environmental control elements 46 to change, enhance, or otherwise have a desired effect on the user's emotional state. By inferring and inducing an individual's emotional state using sensors 14, thermal haptics 46, and/or other environmental control elements, control circuitry 12 may adapt to an individual's current state and may provide a pleasant environment for the individual to maximize the individual's comfort and pleasure.

The example of FIG. 1 in which fabric 10 includes both sensors 14 and output devices 16 is merely illustrative. If desired, fabric 10 may include sensors 14 without any output devices 16, or may include output devices 16 without any sensors 14.

Circuitry included in fabric 10 such as sensor circuitry 14 and output circuitry 16 may be implemented using a mesh that is embedded in fabric 10. The mesh may be formed form a grid of fibers (e.g., solid wires and/or intertwined fibers). The fibers in the grid may be conductive (i.e., the mesh may be a conductive mesh) and/or the fibers in the grid may include non-conducting fibers or portions of fibers.

Figure 2:
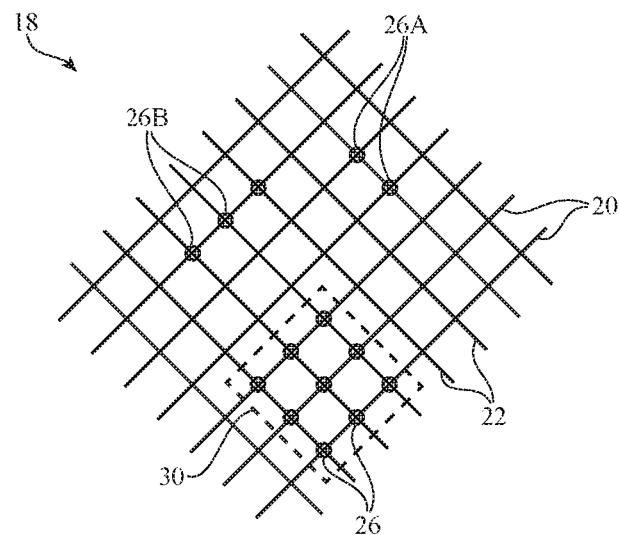
FIG. 2 is a top view of an illustrative conductive mesh that may be embedded in, integrated with, or attached to a fabric-based item in accordance with an embodiment.

FIG. 2 is a top view of an illustrative mesh 18 that may be embedded in fabric 10 of FIG. 1. As shown in FIG. 2, mesh 18 includes a grid of crisscrossing conductive lines 20 and 22. Mesh 18 may be formed from metal, metal fibers, metal fibers that are completely or partly coated with plastic, plastic fibers that are coated with metal or that have metal portions, intertwined fibers (e.g., conductive and/or dielectric fibers), or other suitable conductive and/or insulating materials. If desired, mesh 18 may be formed from a shape memory substance (e.g., nitinol or other shape memory metal alloys, shape memory polymers, etc.).

If desired, mesh 18 may include conductive portions and non-conductive portions. Conductive portions of mesh 18 may be formed from non-conductive threads that are selectively coated with conductive material (e.g., conductive ink, metal coatings, or other conductive materials) and/or may include conductive threads formed form metal filaments (e.g., a collection of metal filaments that are bundled to form a strand). Forming discrete or localized conductive portions on threads may allow portions of mesh 18 to be electrically connected while other portions are in contact but not electrically connected. For example, some overlapping or intersecting portions of mesh 18 may be non-conductive and inactive, whereas other overlapping or intersecting portions of mesh 18 may be selectively coated with conductive material to form an active node 26.

Sensors 14 and output devices 16 may be formed at nodes 26 where lines 20 overlap lines 22 or other suitable locations within fabric 10. Nodes 26 may, for example, correspond to overlapping portions of lines 20 and 22. The portions of lines (fibers) 20 and 22 that overlap at nodes 26 may be coated with insulating coating, may be selectively stripped to form contacts that are coupled to sensors 14 and/or devices 16, may be bare portions of bare wires, etc.

Sensors 14 (FIG. 1) may be formed at nodes 26A, and output devices 16 (FIG. 1) may be formed at nodes 26B. If desired, every node where lines 20 overlap lines 22 may be used for sensing and/or output (e.g., to form an array or sheet of sensors and output devices), or sensing/output nodes may be formed selectively in mesh 18 (e.g., in select regions of mesh 18 such as region 30). The location, number, and density of nodes 26 may be chosen based on the desired sensing or output performance characteristics.

If desired, conductive lines 20 aligned in a first direction may be drive signal lines, and conductive lines 22 aligned in a second direction perpendicular to the first direction may be sense signal lines. Sensing nodes 26A may, for example, include capacitive touch sensing electrodes or the portions of lines 20 and 22 that overlap each other may serve as capacitive touch sensing structures. With this type of arrangement mesh 18 may form a touch sensor. Alternating current drive signals may be driven onto the drive lines. Selected drive signals from the drive lines may be capacitively coupled to one or more sense lines when a user's finger or other body part or other external object (e.g., a stylus, etc.) is present at the intersections between certain drive lines and sense lines. Control circuitry (e.g., control circuitry 12 of FIG. 1) may be used to supply drive signals to electrodes at nodes 26 using drive signal lines 20 and to gather corresponding sense signals using sense signal lines 22. Control circuitry 12 can also process the sense line signals on lines 22 to determine where a user's body is touching mesh 18, etc. If desired, mesh 18 may be used in forming other types of conductive paths (e.g., paths for carrying temperature sensor signals, pressure sensor signals, etc.). The use of mesh 18 for carrying touch sensor signals so that mesh 18 may be used as a two-dimensional touch sensor is merely illustrative.

Sensing nodes 26A and output nodes 26B may be formed in the same region of mesh 18 (e.g., may be adjacent to each other or may be interspersed with one another in a region of fabric 18) or may, if desired, be formed in different regions of mesh 18. The location of sensing nodes 26A and output nodes 26B may depend on the type of garment or other structure that is formed with fabric 10. For example, when fabric 10 is used in forming a shirt or cushion, sensing nodes 26A that are used for temperature sensing may be formed or activated in a location where temperature can be measured most accurately, whereas output nodes 26B that are used for heating and/or cooling may be formed or activated in a location where the body will be receptive to temperature changes (which may be different from the location of sensing nodes 26A). If desired, sensing nodes 26A and output nodes 26B may be activated in the same region or may be activated in different regions.

If desired, sensing nodes 26A and output nodes 26B may be activated individually (e.g., turned on one node at a time), may be activated in groups or regions, or may all be activated at the same time. If desired, nodes in a line may be activated sequentially and/or periodically depending on the type of information being gathered and/or depending on the type of output being provided (e.g., a heating and cooling cycle).

Illustrative examples of activation schemes that may be used to activate sensors 14 of FIG. 1 and/or output devices 16 of FIG. 1 are shown in FIGS. 3A, 3B, 3C, and 3D. Activation schemes of the type shown in FIGS. 3A-3D may be used as output activation schemes (e.g., schemes by which output devices 16 of FIG. 1 are activated and output is provided to a user) or may be used as sensing activation schemes (e.g., schemes by which sensors 14 of FIG. 1 are activated and sensor data is gathered). In the examples of FIGS. 3A-3D, nodes 26' are activate nodes (e.g., nodes that are actively sensing or actively providing output), while nodes 26 are inactive nodes (e.g., nodes that are not gathering sensor data or providing output).

Figure 3A:
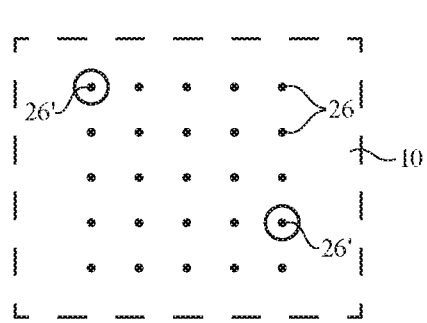
FIGS. 3A, 3B, 3C, and 3D show illustrative examples of activation schemes that may be used to activate sensors or output devices in a fabric-based item in accordance with an embodiment.

In the example of FIG. 3A, one or more individual (e.g., isolated) nodes 26' are active while the remaining nodes 26 in fabric 10 are inactive. Nodes 26' may be activated independently of one another or may be activated in sync with one another. Activating individual nodes in this way may allow output at one location on fabric 10 to be independent from and unaffected by the output at another location on fabric 10.

Figure 3B:
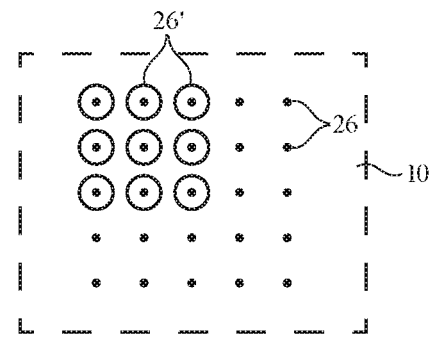

In the example of FIG. 3B, a group or sub-array of nodes 26' is active while the remaining nodes 26 in fabric 10 are inactive. Activating nodes in portions or sub-regions of fabric 10 may be useful in providing output to a particular region of a user's body (e.g., to heat a user's neck or to provide other suitable output to a particular region). In another embodiment, control circuitry 12 may heat, cool, vibrate, or otherwise activate certain nodes when sensors or other devices gather input indicating that those particular nodes should be activated. As an example, a cushion may be heated, cooled, or vibrated only where sensors 12 detect the presence of a user's body or detect the presence of a temperature rise change that exceeds a predetermined threshold.

Figure 3C:
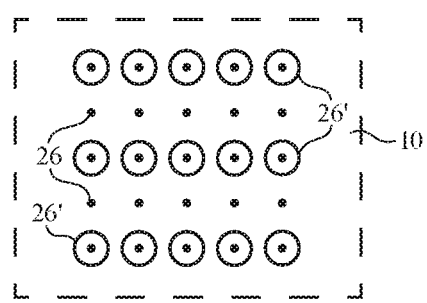

In the example of FIG. 3C, nodes 26' are activated in a particular pattern. This type of activation scheme may include activating all of the nodes 26' in a particular pattern simultaneously, or activating the nodes 26' in the pattern sequentially. For example, a first row of nodes may provide heating for a first period of time, and a second row of nodes may provide heating for a second period of time following the first period of time.

Figure 3D:
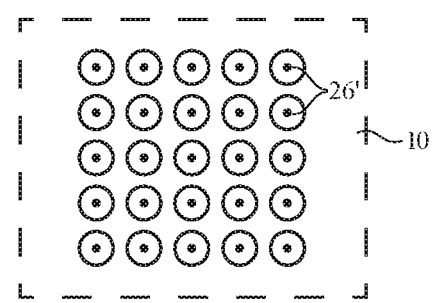

In the example of FIG. 3D, all of nodes 26' in fabric 10 are activated. All of nodes 26' in fabric 10 may be actively sensing to gather information about a user, all of nodes 26' may be actively providing output to the user, or some of nodes 26' may be sensing while other nodes 26' may be providing output.

Figure 4:
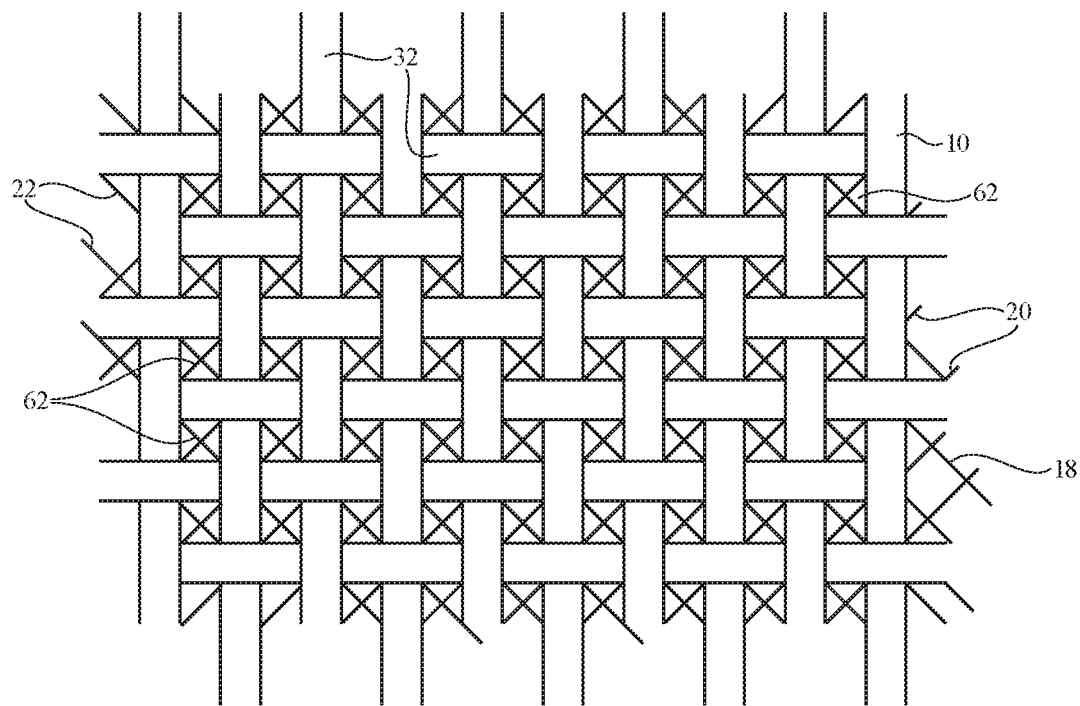
FIG. 4 is a top view of an illustrative fabric-based item that includes woven strands of material in accordance with an embodiment.

FIG. 4 is a top view of fabric 10 showing how mesh 18 of FIG. 2 may be embedded in fabric 10. In the example of FIG. 4, mesh 18 is interwoven with strands 32 of fabric 10. This is, however, merely illustrative. If desired, mesh 18 may be sandwiched between two layers of fabric 10, may be stitched into fabric 10, may be attached to the surface or edge of fabric 10, or may be integrated with fabric 10 using any other suitable method. Mesh 18 may be formed in a single layer in or on fabric 10 or may be separated into multiple layers in or on fabric 10. For example, conductive lines 20 and 22 of mesh 18 may both be formed in a single layer (e.g., a single layer embedded in, surface-mounted on, or integral with fabric 10), or conductive lines 20 of mesh 18 may be formed in a first layer and conductive lines 22 may be formed in a second layer (e.g., portions of fabric 10 may be interposed between lines 20 and lines 22).

Item 10 may include intertwined strands 32. The strands may be intertwined using strand intertwining equipment such as weaving equipment, knitting equipment, braiding equipment, or equipment that intertwines strands by entangling the strands with each other in other ways (e.g., to form felt). Intertwined strands 32 may, for example, form woven or knitted fabric or other fabric (i.e., item 10 may be a fabric-based item), a braided cord, etc.

Strands 32 may be single-filament strands or may be threads, yarns, or other strands that have been formed by intertwining multiple filaments of material together. Strands 32 may be formed from polymer, metal, glass, graphite, ceramic, natural fibers such as cotton, bamboo, wool, or other organic and/or inorganic materials and combinations of these materials. Strands 32 may be entirely insulating, entirely conductive, or partially insulating and partially conductive.

Conductive coatings such as metal coatings may be formed on non-conductive strands (e.g., plastic cores) to make them conductive and strands such as these may be coated with insulation or left bare. Reflective coatings such as metal coatings may be applied to strands 32 to make them reflective. Strands 32 may also be formed from single-filament metal wire, multifilament wire, or combinations of different materials.

Strands 32 may be conductive along their entire length or may have conductive segments (e.g., metal portions that are exposed by locally removing insulation or that are formed by adding a conductive layer to a portion of a non-conductive strand). Threads and other multifilament yarns that have been formed from intertwined filaments may contain mixtures of conductive fibers and insulating fibers (e.g., metal strands or metal coated strands with or without exterior insulating layers may be used in combination with solid plastic strands or natural strands that are insulating).

Item 10 may include additional mechanical structures such as polymer binder to hold strands 32 together, support structures such as frame members, housing structures (e.g., an electronic device housing), and other mechanical structures.

If desired, fabric 10 may include multiple layers or pieces of mesh 18. The layers of mesh 18 may be stacked (e.g., may overlap each other in or on fabric 10) or may be formed in different regions of fabric 10 (e.g., a first mesh in first portion of fabric 10 and a second mesh in a second portion of fabric 10). If desired, multiple layers of fabric 10 may be combined with one or more layers or pieces of mesh 18. For example, layers of fabric 10 may be alternated with layers or pieces of mesh 18.

The breathability of fabric 10 may be determined by the thread density and/or by the size of openings 62 in fabric 10. Fabrics with a tighter weave have lower breathability than fabrics with a looser weave. Adjusting the breathability of fabric 10 be achieved using an actuator system that is based on shape memory material. For example, mesh 18 or other portions of fabric 10 may be formed with or may include portions formed with shape memory material. The shape memory material may be heated by passing a current through the shape memory material using a heating element. Using shape memory effects (e.g., the two-way shape memory effect), the state of fabric 10 may be controlled. For example, a loop-shaped structure may be expanded or contracted when it is desired to locally stretch or relax a portion of fabric 10. Shape memory metal actuators or electromechanical actuators based on solenoids, motors, etc. may also be used in opening and closing air vents, turning on and off fans, or otherwise adjusting components and/or structures associated with fabric 10 that adjust how much heat is generated by fabric 10 and/or passes through fabric 10. If desired, control circuitry 12 can control heating and/or cooling by controlling how much current flows through Peltier effect elements in fabric 10 (and therefore how much heating and/or cooling is produced).

When the shape memory material that forms mesh 18 or other portion of fabric 10 is maintained at room temperature, the shape memory material may have a first shape that places fabric 10 (or a portion of fabric 10) in a first state (e.g., in which openings 62 or larger air vents in fabric 10 have a first size). When the shape memory material that forms mesh 18 or other portion of fabric 10 is heated to an elevated temperature (e.g., a temperature above room temperature), the shape memory material may have a second shape that places fabric 10 or a portion of fabric 10 in a second state (e.g., in which openings 62 or larger air vents in fabric 10 have a second size). In one illustrative example, shape memory material may be embedded in threads 32 and may be used to adjust the diameter of threads 32 or other property of threads 32 to adjust the size of openings 62 or other openings in fabric 10. In another illustrative example, shape memory material may be separate from threads 32 and may be used to tighten or loosen the weave of threads 32 to adjust the size of openings 62.

The breathability of the entire fabric 10 may be adjusted simultaneously or the breathability of fabric 10 or the size of one or more openings in fabric 10 may be adjusted in discrete, localized areas of fabric 10 without affecting the breathability of the remainder of the fabric 10.

Figure 5:
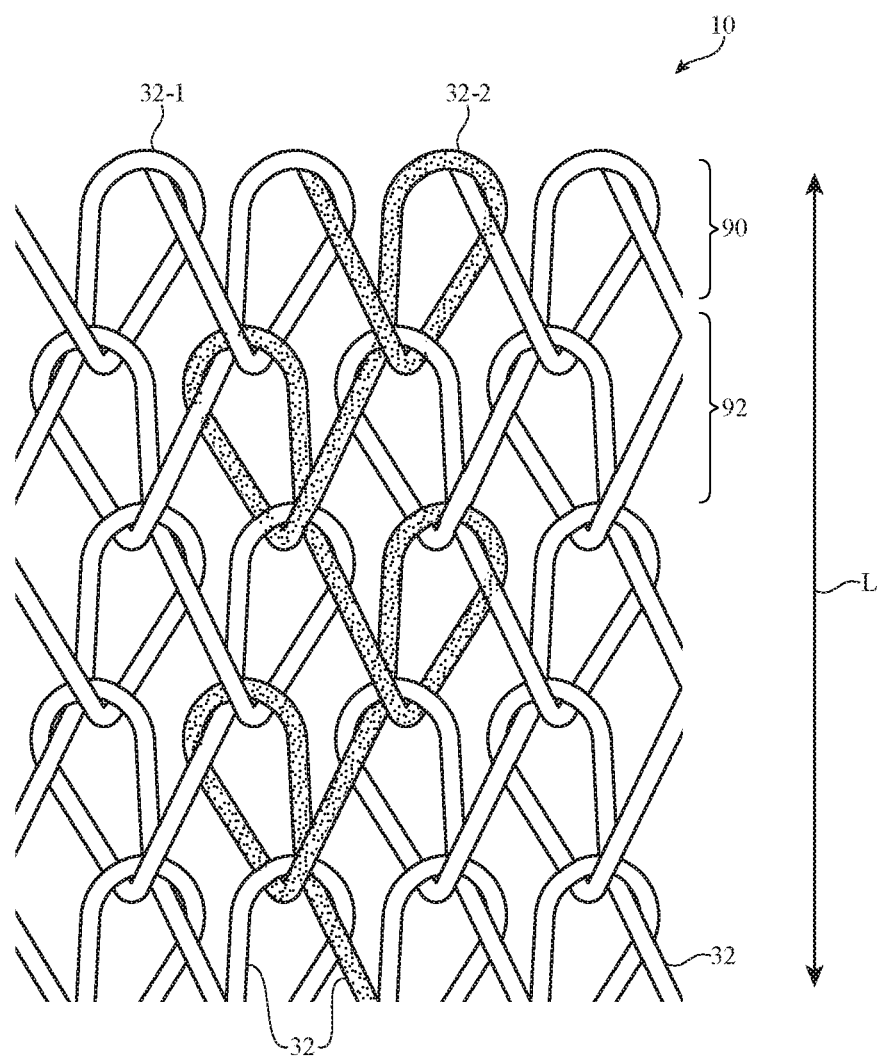
FIG. 5 is a top view of an illustrative fabric-based item that includes warp knit strands of material in accordance with an embodiment.

The example of FIG. 4 in which fabric-based item 10 is formed with woven fabric is merely illustrative. If desired, fabric-based item 10 may be a warp knit fabric, as shown in FIG. 5. In the example of FIG. 5, fabric 10 is a warp knit fabric having columns of warp strands 32 that zigzag along the length L of fabric 10. Each warp strands 32 has a number of loops, with each loop securing a loop of an adjacent strand 32 from a previous row. For example, the loops of row 92 in fabric 10 secure the loops of row 90 in fabric 10.

If desired, sensing components 14 and output components 16 may be incorporated into strands 32 of fabric 10. For example, sensing components 14 and/or output components 16 may be formed using non-conductive strands 32-1 and conductive strands 32-2 in fabric 10.

The fabrics of FIGS. 4 and 5 are merely illustrative. In general, fabric 10 may have a plain weave, a satin weave, a twill weave, or variations of these weaves, may be a three-dimensional woven fabric, or may be other suitable woven fabric. If desired, the strands that make up item 10 may be intertwined using knitting equipment, braiding equipment, or other strand intertwining equipment. Item 10 may also incorporate more than one type of fabric or intertwined strand-based material (e.g., item 10 may include both woven and knitted portions).

Fabric 10 may be used to form an article of clothing, a wrist band, a backpack or other bag, or other items such as a seat cushion. For example, fabric 10 may be used to form a cushion that can be moved between one or more pieces of furniture, a cushion that is formed as part of a chair, sofa, or other seating, a cushion that is built into a seat in a car, airplane, train, or other vehicle, a cushion that is part of medical equipment, a cushion that is part of a wheel chair, or other seating. When fabric 10 is formed as part of a cushion, then sensors of fabric 10 or other input devices can provide control circuitry 12 with information that control circuitry 12 processes to determine how to adjust output devices 16. For example, if control circuitry 12 detects pressure or temperature changes in a particular portion of a cushion, control circuitry 12 can direct output devices 16 to make corresponding temperature changes, vibrations, or other adjustments (e.g., to enhance user comfort, etc.). The corresponding output may be provided at the same location of fabric-based item 10 that the pressure or temperature change was detected or may be at a different location of fabric-based item 10.

Figure 6:
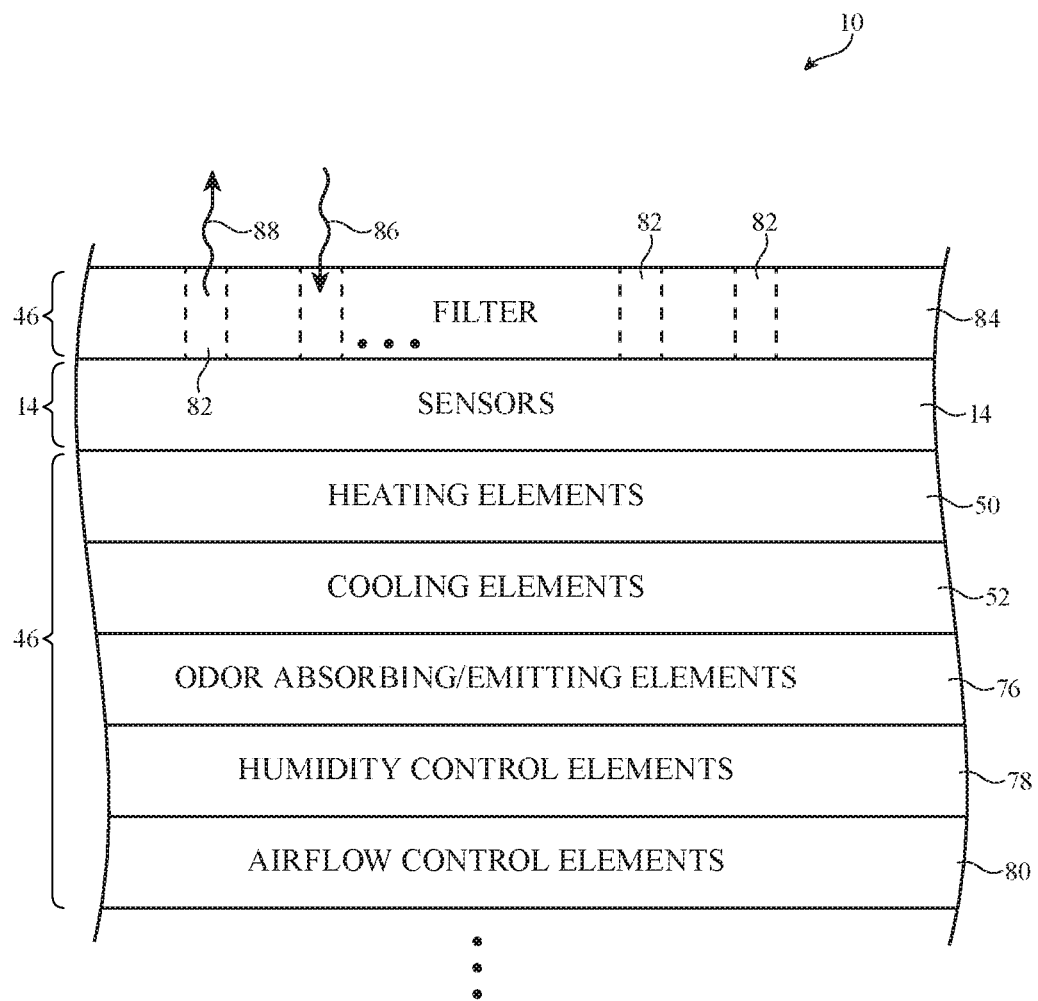
FIG. 6 is a cross-sectional side view of an illustrative fabric-based item that includes a filter layer and one or more environmental control layers in accordance with an embodiment.
Figure 7:
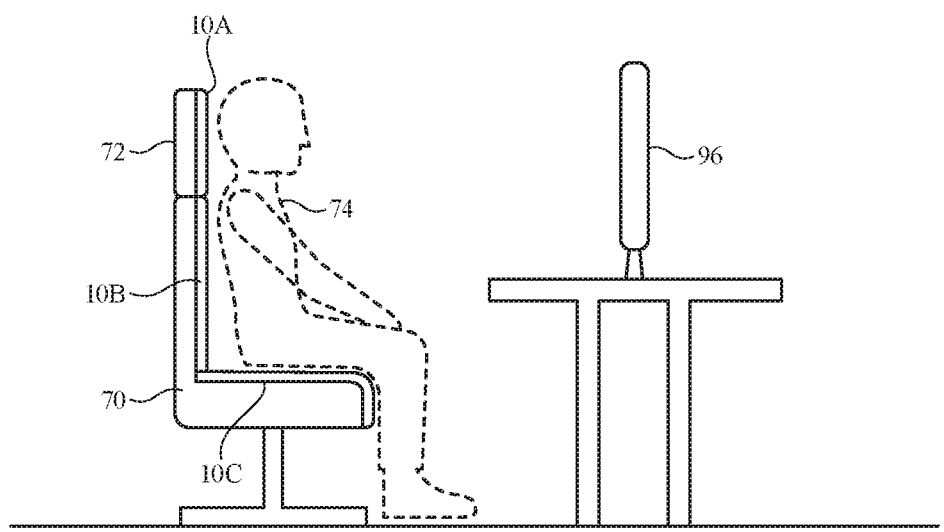
FIG. 7 is a side view of an illustrative vehicle with a fabric-based environmental control system in accordance with an embodiment.

Fabric-based item 10 may include one or more layers of sensing elements 16 and one or more layers of environmental control elements 46. As shown in FIG. 6, for example, fabric-based item 10 may include one or more environmental control layers 46 and sensing layers 14. Environmental control layers 46 and sensing layers 14 may be stacked layers with each layer containing a different sensor or environmental control element, or any two or more of environmental control layers 46 and sensing layers 14 may be integrated into one layer. There may be some regions of fabric 10 that include less than all of the layers shown in FIG. 6 or the entirety of fabric 10 may include all of the layers shown in FIG. 6. The example of FIG. 6 in which each layer contains a different sensing or environmental control element is merely illustrative. The layers of FIG. 6 may be embedded in layers of intertwined strands 32 that make up fabric 10, may be sandwiched between layers intertwined strands 32 that make up fabric 10, may be formed on or otherwise attached to layers of intertwined strands 32 that make up fabric 10, or may be formed entirely or partially from intertwined strands 32 that make up fabric 10.

As shown in FIG. 6, environmental control elements may include a filter or screen layer 84, heating elements 50, cooling elements 52, odor absorbing and/or odor emitting elements 76, humidity control elements 78, airflow control elements 80, and/or other suitable structures or output devices for changing or maintaining the environment around fabric 10 for a user or for providing various sensations to the user.

Airflow control elements 80 may include fans or other structures that push air 88 out of fabric 10 and/or may include structures that pull air 86 into fabric 10. Air 88 may be directed directly at a user or may provide indirect environmental control for the user. Humidity control elements 78 may be used to adjust humidity levels in the environment around the user (e.g., by adjusting the amount of moisture provided to the environment). Humidity control elements 78 may include desiccants or other moisture absorbing materials and/or may include humidifiers that release moisture into the environment around the user. If the humidity of the environment around a user is low, control circuitry 12 may use humidity control elements 78 to vaporize liquid water and thereby humidify the environment around fabric 10 and the user. Odor emitting and odor absorbing elements 76 may be used to provide a scent to the environment and/or to absorb odors from the environment around the user. Odor absorbing elements in layer 76 may include charcoal or other odor absorbing materials. Odor emitting elements in layer 76 may include naturally or artificially scented materials that release a pleasant scent into the environment around the user.

Filter layer 84 may include air passageways such as openings 82 through which air may pass through filter 84. Openings 82 may allow air 88 to escape from fabric-based item 10 and air 86 to pass into fabric-based item 10. Openings 82 may be openings in a layer of fabric (e.g., similar to openings 62 of FIG. 4), may be openings in a metal mesh structure, or may be openings in a layer of plastic, metal, ceramic, glass, or other suitable material. Control circuitry 12 may be configured to control the size of openings 82 to control the amount of air that passes through filter 84. For example, control circuitry 12 may switch openings 82 between opened and closed states and/or may adjust the size with which openings 82 are opened.

Filter 84 may be used to control when and how quickly external elements such as air, odors, and moisture are absorbed into fabric 10 and when and how quickly internal elements such as air from airflow control elements 80, moisture from humidity control elements 78, and odor from odor emitting elements 76 escape from fabric 10. If desired, odor emitting and absorbing elements 76 may be used in conjunction with airflow control elements 80 to enhance the effect of odor emitting and absorbing elements 76. For example, odor emitting elements 76 may include a scented substance and airflow control elements 80 may push air 88 through the scented substance in layer 76 so that scented air 88 escapes through holes 82.

Adaptive fabrics that adapt to an individual's biometric state to create a desired environment for the individual may be incorporated into seat covers or furniture on which the individual sits. In one illustrative example, the bio-adaptive fabric may be incorporated into a cover or cushion for a car seat in a vehicle. A side view of an illustrative vehicle of the type that may be provided with fabrics having environmental control elements is shown in FIG. 1. As shown in FIG. 1, vehicle 40 (e.g., a system of the type shown and described in connection with FIG. 1) may include a body such as body 66. Body 66 may have body panels and other structures that are mounted on a chassis. Interior components in vehicle 40 such as seating for a driver and other vehicle occupants may be supported by the chassis (see, e.g., front vehicle seat 70F for supporting a user such as vehicle occupant 74 and rear seat 70R which may support additional passengers). External components such as wheels 64 may also be mounted to the chassis. The structures that make up body 66 may include metal structures, structures formed from fiber-composite materials such as carbon-fiber materials and fiber-glass, plastic, and other materials.

Vehicle body 66 may include doors. Windows may be formed at the front and rear of vehicle 40 in openings in body 66 and may be formed within the doors or other portions of the body 66 of vehicle 40. For example, vehicle 40 may have a front window that faces the front of vehicle 40 and rearward facing windows and side windows mounted within the doors of vehicle 40. Windows in vehicle 40 may be formed from glass (e.g., glass laminated with polymer layers), plastics such as polycarbonate, or other clear materials.

The structures of vehicle 40 such a body 66 define an interior region such as vehicle interior 68. The characteristics of interior 68 adjacent to passengers such as passenger 74 (e.g., temperature, air flow, scent, humidity, etc.) may be adjusted using bio-adaptive fabric-based seat portions such as fabric portion 10A in head rest 72, fabric portion 10B in a back portion of seat 70F, and fabric portion 10C in a lower portion of seat 70F. Fabric portion 10A may be adjacent to the head of user 74, fabric portion 10B may be adjacent to the back and shoulders of user 74, and fabric portion 10C may be adjacent to the lower body of user 74. Adaptive fabrics 10A, 10B, and 10C may include sensors 14 and environmental control elements 46 (e.g., as described in connection with FIGS. 1-6).

Control circuitry 12 (FIG. 1) may operate fabric portions 10A, 10B, and 10C in unison or may operate fabric portions 10A, 10B, and 10C individually to provide different sensing schemes and output schemes around different areas of the body of user 74. As an example, sensors 14 in fabric 10B may be configured to measure body temperature around the underarms of user 74. Control circuitry 12 may infer an emotional state of user 74 from the body temperature information and may activate environmental control elements 46 in fabric portion 10A, 10B, and/or 10C to provide cooling, heating, humidity adjustment, airflow adjustment, odor adjustment, or other environmental adjustment to the environment around user 74 in those regions. Control circuitry 12 may initiate a thermal program or cycle in which various environmental adjustments are made by environmental control elements 46 in fabric portions 10A, 10B, and 10C to create the desired environment around the user's body in response to the detected biometric state of user 74.

If desired, other structures or electronic devices in vehicle 40 may supplement or use the information gathered by sensors 14 in fabric 10 to further enhance the environment around user 74. For example, a camera, gaze detection device, or other sensor in vehicle 40 may provide user information (e.g., information about the user's gaze or eyelids, information about the user's facial expressions, or other information that may be used to infer the user's biometric state) to control circuitry 12 to supplement the information gathered by sensors 14 in fabric 10. Control circuitry 12 may use the user information from other sensors in vehicle 40 in conjunction with the information from sensors 14 in fabric 10 to determine a biometric state of user 74. Control circuitry 12 may activate environmental control elements 46 based on the biometric state of user 74.

Just as control circuitry 12 may use other sensors in vehicle 40 to supplement or replace sensor data from sensors 14 in fabric 10, other control circuitry 12 may, if desired, use other output devices in vehicle 40 to supplement or replace the output from environmental control elements 46 in fabric 10. For example, the characteristics of interior 68 (e.g., sounds, air temperature, air flow, scent, humidity, etc.) may be adjusted by an environmental control system in vehicle 10 (e.g., in a dashboard region or elsewhere in vehicle 40) in response to sensor information gathered by sensors 14 in fabric 10 and/or gathered by other sensors in vehicle 40. The output may be provided by an air conditioning and heating unit that produces heated and/or cooled air in response to biometric information from sensors 14, a sound system that provides sound to user 74 in response to biometric information from sensors 14, and/or other environmental control devices that can adjust or maintain the environment around user 74 based on biometric information from sensors 14 in fabric portions 10A, 10B, and 10C.

The location of fabric portions 10A, 10B, and 10C in vehicle 40 are merely illustrative. If desired, bio-adaptive fabric 10 may be located on one or more armrests, a seat belt, the interior surface of a door, a steering wheel, or other suitable location in vehicle 40.

Figure 8:
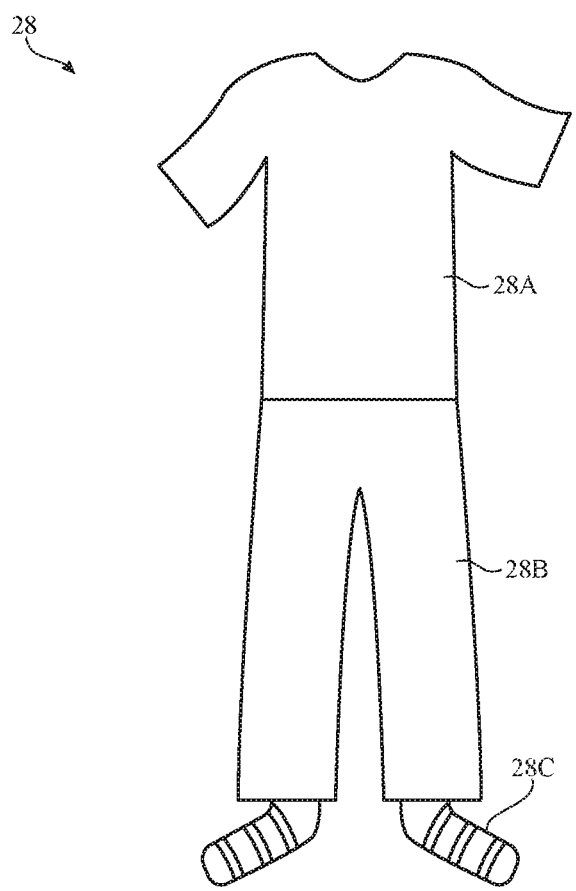
FIG. 8 is a diagram showing illustrative articles of clothing which may include environmental control elements in accordance with an embodiment.

If desired, bio-adaptive fabric 10 may be incorporated into one or more articles of clothing. Illustrative articles of clothing 28 which may be formed using fabric 10 are shown in FIG. 8. Fabric 10 may be used to form shirts 28A, pants 28B, or socks 28C. This is, however, merely illustrative. In general, fabric 10 may be used to form any suitable article of clothing and/or may be used in forming other structures that a user touches, uses, or interacts with. For example, fabric 10 may be used to form a seat cushion, a back cushion, a neck pillow, a blanket, an arm band, a watch band, a leg band, a head band, a hat, an article for securing a portable electronic device, etc.

FIGS. 9A, 9B, 9C, 9D, and 9E show illustrative ways in which sensors and environmental control elements may be incorporated into articles of clothing. In these examples, sensors 14 and environmental control elements 46 are represented by conductive mesh 18. However, it should be understood that not all of the sensors and output devices in fabric 10 may be formed using a conductive mesh. In the examples of FIGS. 9A-9E, fabric 10 is used to form a t-shirt 28. However, it should be understood that fabric 10 may be used in forming any other suitable garment or article.

Figure 9A:
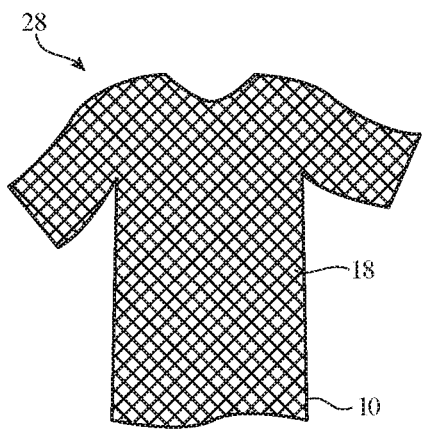
FIGS. 9A, 9B, 9C, 9D, and 9E show illustrative ways in which sensors and environmental control elements may be incorporated into a fabric-based article of clothing in accordance with an embodiment.

In the example of FIG. 9A, mesh 18 is embedded throughout fabric 10.

Figure 9B:
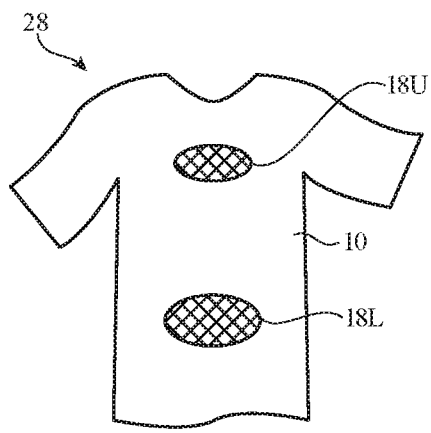

In the example of FIG. 9B, mesh 18 is embedded in select portions of fabric 10. For example, upper mesh 18U may be used to cool or heat a user's upper back area, while lower mesh 18L may be used to cool or heat a user's lower back area (as an example).

Figure 9C:
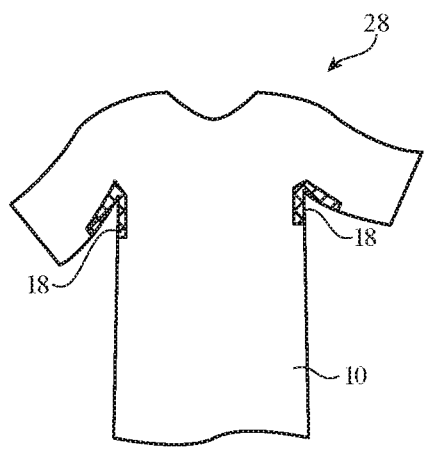

In the example of FIG. 9C, mesh 18 is embedded in select portions of fabric 10 such as portions that cover a user's under arms. Mesh 18 in these regions may, for example, detect perspiration using sensing nodes 26A and provide cooling using output nodes 26B.

Figure 9D:
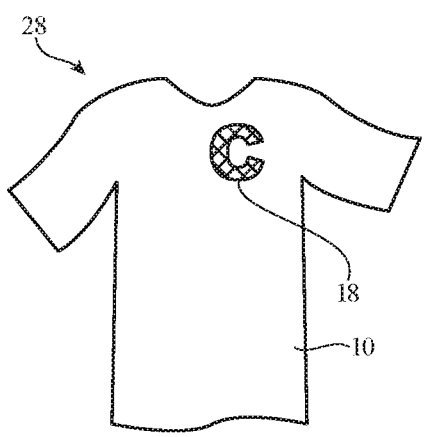

In the example of FIG. 9D, mesh 18 has been incorporated into a logo or emblem on shirt 28. If desired, mesh 18 that is incorporated into a logo or emblem may be sewn or otherwise attached to a normal shirt (e.g., a shirt without any embedded mesh 18).

Figure 9E:
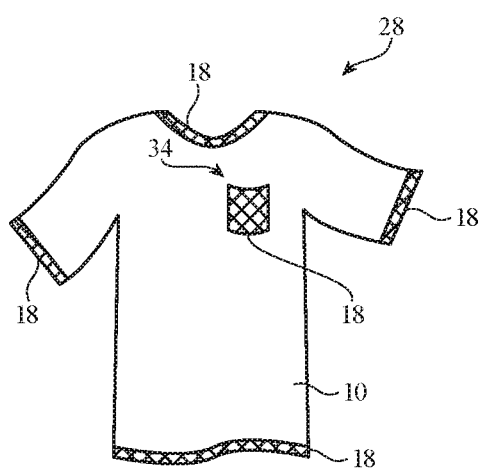

In the example of FIG. 9E, mesh 18 is incorporated into regions of shirt 28 with thicker fabric. For example, mesh 18 may be incorporated into the seams at the edges of shirt 28 or the seams around pocket 34 of shirt 28. Forming mesh 18 using thicker portions of fabric 10 may allow components such as sensors 14, output devices 16, and/or control circuitry 12 (e.g., a microprocessor, etc.) to be formed in fabric 10 without being visibly present to a user. For example, portions of the seams of fabric 10 that include sensing circuitry 14, output circuitry 16, or control circuitry 12 may have the same thickness as portions of the seams with fabric only (e.g., without any embedded circuitry). Hiding the circuitry in fabric 10 in this way may help to maintain the desired aesthetics of shirt 28 without sacrificing functionality.

Figure 10:
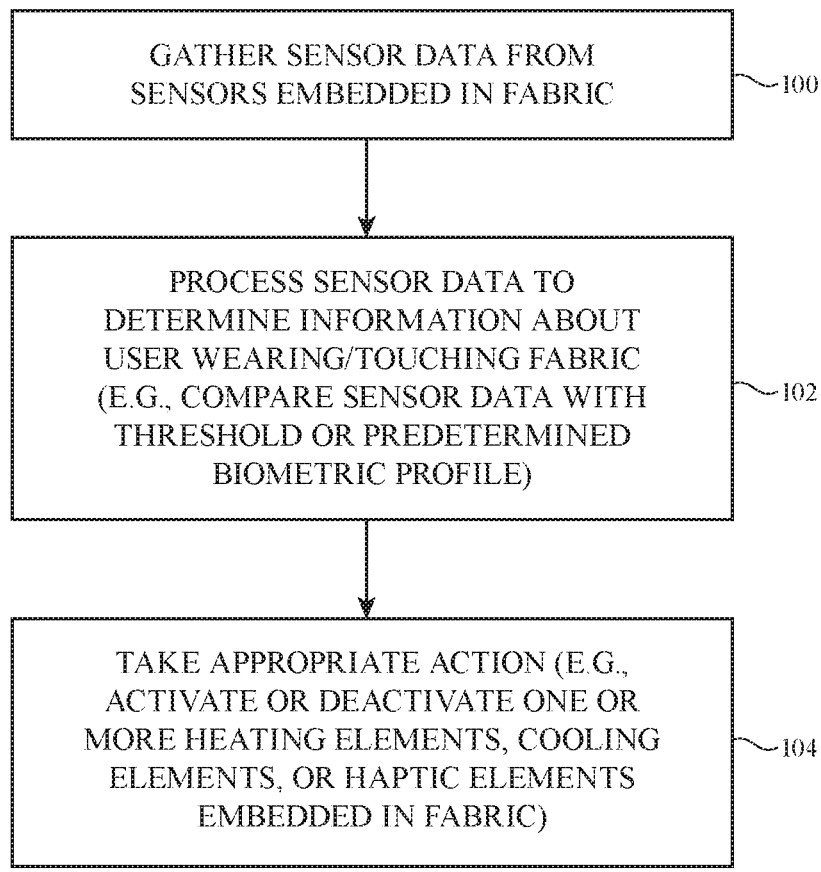
FIG. 10 is a flow chart of illustrative steps in operating a fabric-based item with environmental control elements in accordance with an embodiment.

FIG. 10 is a flow chart of illustrative steps involved in operating a fabric-based system (e.g., system 40 of FIG. 1) having a fabric with embedded sensors and environmental control elements.

At step 100, control circuitry 12 may gather information to use when controlling fabric 10. For example, control circuitry 12 can gather user input such as user commands. The user commands can be touch gestures, button presses, voice commands, or other input. Circuitry 12 may also gather sensor data from sensors 14 embedded in fabric 10 and/or other sensors. This may include, for example, gathering temperature information from one or more temperature sensors, moisture information from one or more moisture detectors or humidity sensors, pulse information from a pulse sensor, heart rate information from a heart rate sensor, etc. Control circuitry 12 may use information on the operating environment of fabric 10, time and date information, location information, and/or other information in controlling fabric 10. Control circuitry 12 may gather information from other sensors that are not integrated with fabric 10 (e.g., one or more cameras that track the gaze or facial expression of a user). The use of sensor input from sensors 14 is merely illustrative.

At step 102, control circuitry 12 may process the gathered sensor data and/or other information to assess the condition of the user's experience or body. This may include, for example, comparing the gathered sensor data (e.g., gathered biometric information) with a threshold or a predetermined standard or biometric profile, recognizing commands, processing environmental data such as ambient temperature data, etc. Other processing may include averaging sensor data from a single sensor to obtain a final measurement value. For example, control circuitry 12 may average temperature readings from temperature sensors in two or more locations in fabric 10 to obtain an average skin or body temperature. Other processing may include combining sensor data from different types of sensors in fabric 10 or other sensors to determine certain information about a user's biometric state. For example, a first sensor in fabric 10 may detect high temperatures and a second sensor in fabric 10 may detect swelling, which may be indicative of an injury (as an example). If desired, control circuitry 12 may infer the user's emotional state based on the biometric data. For example, elevated temperatures in certain areas of the body may be indicative of stress. Gaze information from a camera may indicate sleepiness (as an example).

If desired, sensor data or other data may be gathered from different devices and/or fabric structures. For example, data may be gathered by a first fabric item (clothing, wrist band, head band, cushion, etc.) and may be gathered by a second fabric item (clothing, wrist band, head band, cushion, etc.). The gathered data from one or more items may be used locally (e.g., in the item that gathered the data) or may be used by another item. For example, data gathered by one item of clothing such as a shirt may be used in controlling output devices 16 in another item of clothing such as a pair of pants. Data may be processed using control circuitry in one or more of the items (e.g., electrical devices and/or fabric-based devices such as clothing, cushions or other seating structures, etc.).

At step 104, system 40 may take appropriate action based on the information gathered at step 102. For example, control circuitry 12 may issue control signals to output devices 16 to activate or deactivate one or more of heating elements 50, cooling elements 52, vibrators or other mechanical actuators such as haptic elements 54, or other environmental control elements 46. The output devices may be used to heat fabric 10, cool fabric 10, shrink or stretch fabric 10, vibrate fabric 10, adjust the breathability of fabric 10, or perform other suitable functions to adjust the user's sensation or experience (e.g., to adjust skin or body temperature, to adjust blood circulation, to alert a user, to adjust pleasurability, etc.). As examples, if overheating is detected, fabric 10 may be cooled using cooling elements 50. If an injury is detected, a physical therapy program may be initiated (e.g., the affected area may be heated, cooled, compressed, etc.).

The example described above in which control circuitry 12 operates output devices 16 in response to information from sensors 14 is merely illustrative. If desired, the operations of step 104 may be performed automatically or may be pre-programmed to occur. For example, output devices 16 may provide output independently of the data gathered by sensors 14, or fabric 10 may not include any sensors 14 and fabric 10 may be used as a programmable fabric with programmable temperature control features.

The foregoing is merely illustrative and various modifications can be made by those skilled in the art without departing from the scope and spirit of the described embodiments. The foregoing embodiments may be implemented individually or in any combination.

What is claimed is:

1. A system, comprising:
   a fabric comprising intertwined strands of material, wherein the strands of material include electrically conductive strands and electrically insulating strands;
   sensors in the fabric that gather biometric information about a user;
   temperature control elements in the fabric, wherein the temperature control elements include a first temperature control element that controls a temperature of a first region of the fabric and a second temperature control element that controls a temperature of a second region of the fabric; and
   control circuitry that receives the biometric information from the sensors via the electrically conductive strands and that operates the temperature control elements based on the biometric information, wherein the control circuitry operates the first and second temperature control elements independently of one another and determines whether to activate the first temperature control element or the second control element based on the biometric information gathered by the sensors.

2. The system defined in claim 1 wherein the sensors comprise temperature sensors.

3. The system defined in claim 1 wherein the temperature control elements comprise at least one Peltier effect device.

4. The system defined in claim 1 wherein the sensors are located in a third region of the fabric that is different than the first and second regions.

5. The system defined in claim 1 wherein the fabric includes openings and wherein the control circuitry adjusts a size of the openings based on the biometric information.

6. The system defined in claim 1 wherein the fabric comprises an odor absorbing layer.

7. The system defined in claim 1 further comprising humidity control elements in the fabric that adjust an amount of moisture in a vicinity of the fabric, wherein the control circuitry operates the humidity control elements based on the biometric information.

8. The system defined in claim 1 wherein the sensors comprise at least one humidity sensor.

9. The system defined in claim 1 wherein the sensors comprise at least one heart rate sensor.

10. The system defined in claim 1 wherein the fabric comprises a warp knit fabric.

11. An environmental control system that controls an environment for a passenger in a vehicle, comprising:
    a fabric on which the passenger sits, wherein the fabric comprises electrically conductive strands intertwined with electrically insulating strands;
    at least one temperature sensor in the fabric that measures a temperature of the passenger;
    at least one environmental control element in the fabric that provides different sensations to the passenger; and
    control circuitry that operates the at least one environmental control element based on the temperature of the passenger, wherein the control circuitry receives signals from the at least one temperature sensor via the electrically conductive strands.

12. The environmental control system defined in claim 11 wherein the vehicle has an interior and wherein the at least one environmental control element comprises a humidity control element that adjust an amount of moisture in the interior of the vehicle.

13. The environmental control system defined in claim 11 wherein the at least one environmental control element comprises a Peltier effect device that adjusts a temperature of the fabric.

14. The environmental control system defined in claim 11 wherein the vehicle has an interior and wherein the at least one environmental control element comprises an odor emitting layer that releases a scent into the interior of the vehicle.

15. The environmental control system defined in claim 11 wherein the fabric has openings and wherein the at least one environmental control element comprises an airflow control element that controls how much air passes through the openings in the fabric.

16. A method for operating an adaptive fabric that adapts to an individual's biometric state, wherein the adaptive fabric comprises electrically conductive strands intertwined with electrically insulating strands, the method comprising:
    with a sensor in the fabric, gathering biometric information from the individual;
    with control circuitry:
        receiving the biometric information from the sensor via the electrically conductive strands, and
        activating a thermal haptic device in the fabric in response to the biometric information from the sensor; and
    with the thermal haptic device, changing a thermal property of the fabric in response to being activated.

17. The method defined in claim 16 wherein the thermal haptic device comprises a Peltier effect device and wherein changing the thermal property of the fabric comprises using the Peltier effect device to change a temperature of the fabric.

18. The method defined in claim 16 wherein the sensor comprises a temperature sensor and wherein gathering biometric information comprises measuring a temperature of the individual.

19. The method defined in claim 16 wherein the thermal haptic device is located in a first region of the fabric and wherein the sensor is located in a second region of the fabric that is different than the first region.

20. The method defined in claim 16 further comprising:
    with the control circuitry, determining an emotional state of the individual based on the biometric information, wherein activating the thermal haptic device in the fabric in response to the biometric information comprises activating the thermal haptic device in the fabric based on the inferred emotional state of the individual.

* * * * *